US007754187B2

(12) United States Patent
Cao et al.

(10) Patent No.: US 7,754,187 B2
(45) Date of Patent: *Jul. 13, 2010

(54) SYNTHESIS OF CHABAZITE-CONTAINING MOLECULAR SIEVES AND THEIR USE IN THE CONVERSION OF OXYGENATES TO OLEFINS

(75) Inventors: Guang Cao, Branchburg, NJ (US); Machteld M. Mertens, Boortmeerbeek (BE); Anil S. Guram, San Jose, CA (US); Hailian Li, Fremont, CA (US); Jeffrey C. Yoder, San Jose, CA (US)

(73) Assignee: ExxonMobil Chemical Patents Inc., Houston, TX (US)

( * ) Notice: Subject to any disclaimer, the term of this patent is extended or adjusted under 35 U.S.C. 154(b) by 456 days.

This patent is subject to a terminal disclaimer.

(21) Appl. No.: 11/820,908

(22) Filed: Jun. 21, 2007

(65) Prior Publication Data

US 2008/0045767 A1 Feb. 21, 2008

Related U.S. Application Data

(63) Continuation-in-part of application No. 11/521,155, filed on Sep. 14, 2006, now Pat. No. 7,670,589.

(60) Provisional application No. 60/731,846, filed on Oct. 31, 2005.

(51) Int. Cl.
*C01B 37/02* (2006.01)
*C01B 39/04* (2006.01)
(52) U.S. Cl. .................................. 423/706; 423/703
(58) Field of Classification Search ................ 423/703, 423/706
See application file for complete search history.

(56) References Cited

U.S. PATENT DOCUMENTS

| | | | |
|---|---|---|---|
| 4,544,538 A | 10/1985 | Zones | |
| 4,610,854 A * | 9/1986 | Zones | 423/706 |
| 5,958,370 A | 9/1999 | Zones et al. | |
| 6,334,994 B1 | 1/2002 | Wendelbo et al. | |
| 6,680,278 B2 | 1/2004 | Cao et al. | |
| 6,709,644 B2 | 3/2004 | Zones et al. | |
| 6,812,372 B2 | 11/2004 | Janssen et al. | |
| 6,984,765 B2 * | 1/2006 | Reyes et al. | 585/639 |
| 7,094,389 B2 * | 8/2006 | Cao et al. | 423/706 |
| 2003/0069449 A1 * | 4/2003 | Zones et al. | 564/463 |
| 2003/0176751 A1 * | 9/2003 | Strohmaier et al. | 585/639 |
| 2003/0232006 A1 * | 12/2003 | Cao et al. | 423/705 |
| 2004/0253163 A1 * | 12/2004 | Cao et al. | 423/305 |
| 2007/0043249 A1 * | 2/2007 | Cao et al. | 585/639 |

FOREIGN PATENT DOCUMENTS

| | | |
|---|---|---|
| EP | 613 859 A | 9/1994 |
| GB | 868846 | 5/1961 |
| WO | WO 95/05342 | 2/1995 |
| WO | WO 98/15496 | 4/1998 |
| WO | WO 02/070407 | 9/2002 |
| WO | WO 03/078324 | 9/2003 |

OTHER PUBLICATIONS

Wilson, S. T. "*Templating in Molecular Sieve Synthesis*" Verified Syntheses of Zeolitic Materials, 2001, 2nd Edition, pp. 27-30. http://www.iza-online.org/synthesis/VS_2ndEd/Templating.htm.
Yuen, L. et al. "*Product selectivity in methanol to hydrocarbon conversion for isostructural compositions of AFI and CHA molecular sieves*," Microporous Materials 2, pp. 105-117, Elsevier Science B.V. Amsterdam (1994).
Barrer, R. et al., "The Hydrothermal Chemistry of the Silicates, Part VII. Synthetic Potassium Aluminosilicates," J. Chem. Soc, pp. 2882-2891 (1956).
Diaz-Cabanas, M. et al. "*Synthesis and structure of pure SiO2 chabazite: the SiO2 polymorph with the lowest framework density*," Chem. Commun., pp. 1881-1882 (1998).
Skeels, G.W. et al, "*Synthesis and Characterization of Phi-Type Zeolites LZ-276 and LZ-277: Faulted Members of the ABC-D6R Family of Zeolites*", Microporous Mesoporous Mater; Microporous and Mesoporous Materials 1999 Elsevier Sci B.V., Amsterdam, Netherlands, vol. 30, No. 2, 1999, pp. 335-346.
Bateman, Charles A. et al, "*Structure of Zeolite LZ-277*", Proc. Annu. Meet Microsc. Soc. Am.; Proceedings—Annual Meeting, Microscopy Society of America 1994, 1994, pp. 784-785.
Wagner, Paul et al, "*Guest/Host Relationships in the Synthesis of the Novel Cage—Based Zeolites SSZ-35, SSZ-36, and SSZ-39*", Journal of the American Chemical Society 2000, 122(2), pp. 263-273.
Dahl, I. et al "*Structural and chemical influences on the MTO reaction: a comparison of chabazite and SAPO-34 as MTO catalysts*," Microporous and Mesoporous Materials 29, pp. 185-190, Elsevier Science B.V. (1999).

* cited by examiner

*Primary Examiner*—David M Brunsman
(74) *Attorney, Agent, or Firm*—Kevin M. Faulkner; David M. Weisberg

(57) ABSTRACT

A method is disclosed of synthesizing a crystalline material comprising a CHA framework type molecular sieve and having a composition involving the molar relationship:

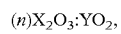

$(n)X_2O_3:YO_2$, wherein X is a trivalent element; Y is a tetravalent element; and n is from 0 to less than 0.01. The method comprises preparing a reaction mixture capable of forming said material, said mixture comprising a source of water, a source of an oxide of a tetravalent element Y and optionally a source of an oxide of a trivalent element X, wherein the reaction mixture is substantially free of fluoride ions added as HF; maintaining the reaction mixture under conditions sufficient to form crystals of the crystalline material; and than recovering the crystalline material. The reaction mixture comprises either a specific directing agent for directing the formation of a CHA framework type molecular sieve and/or a $H_2O:YO_2$ molar ratio of greater than 20. In one embodiment, the resultant crystalline material is free of stacking faults and/or any intergrown phase with an AEI framework type molecular sieve.

20 Claims, 6 Drawing Sheets

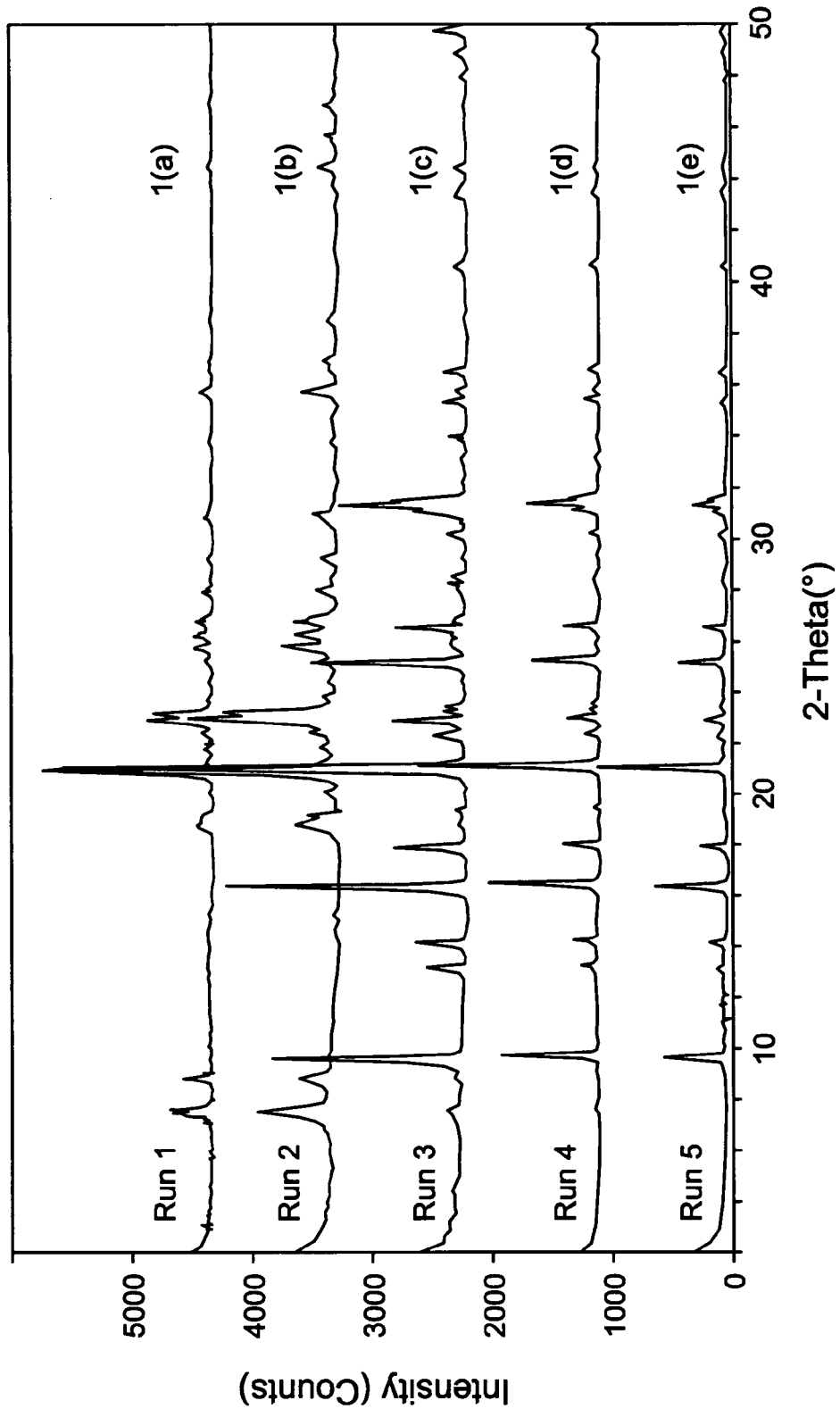

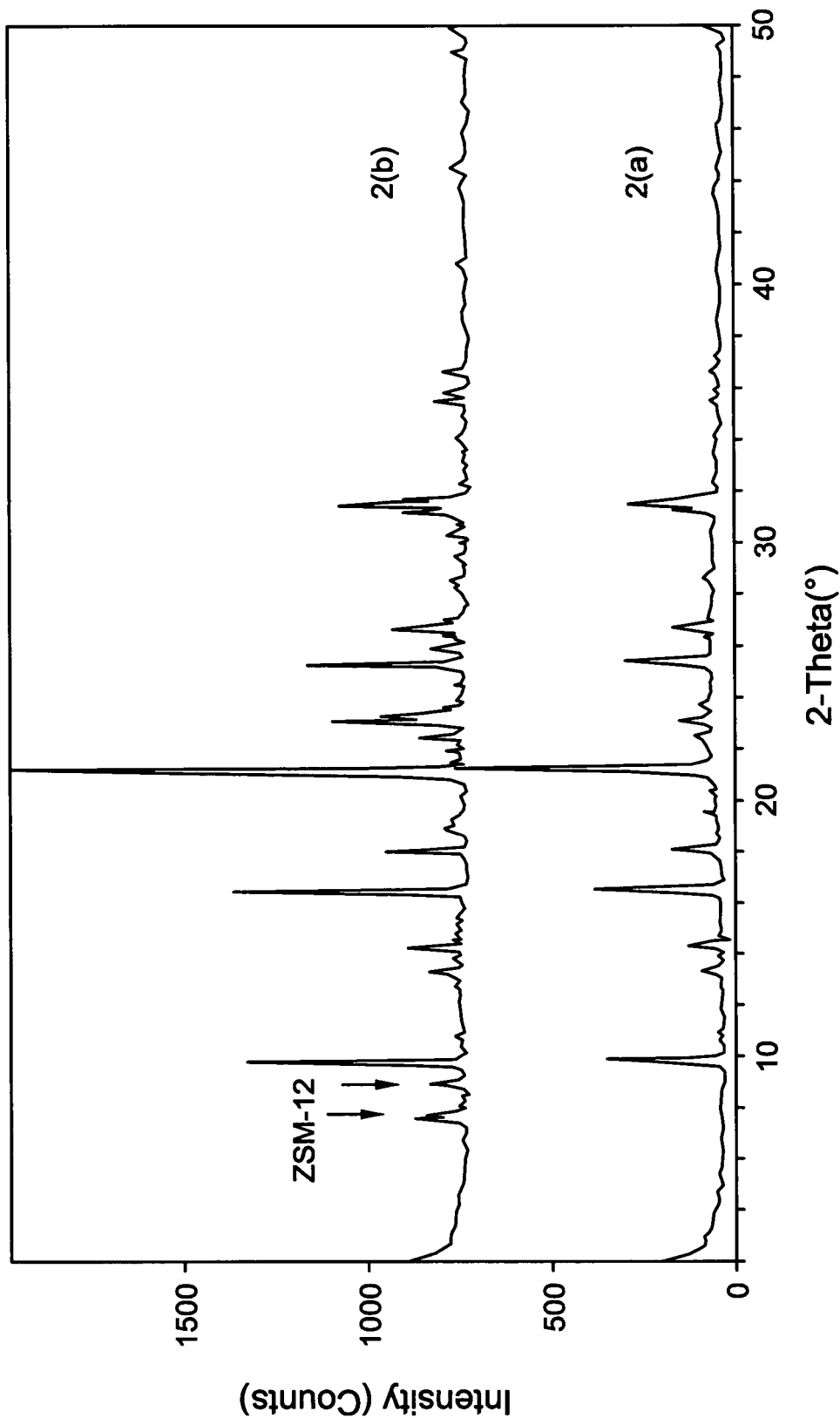

SYNTHESIS OF CHABAZITE-CONTAINING MOLECULAR SIEVES AND THEIR USE IN THE CONVERSION OF OXYGENATES TO OLEFINS

CROSS-REFERENCE TO RELATED APPLICATIONS

This application is a continuation-in-part of U.S. patent application Ser. No. 11/521,155, filed Sep. 14, 2006, now U.S. Pat. No. 7,670,589, which claims priority to U.S. Provisional Patent Application No. 60/731,846, filed Oct. 31, 2005, which is hereby incorporated by reference.

FIELD

This invention relates to the synthesis of chabazite-containing molecular sieves and their use in the conversion of oxygenates, particularly methanol, to olefins, particularly ethylene and propylene.

BACKGROUND

The conversion of oxygenates to olefins (OTO) is currently the subject of intense research because it has the potential for replacing the long-standing steam cracking technology that is currently the industry standard for producing world scale quantities of ethylene and propylene. The very large volumes involved suggest that substantial economic incentives exist for alternate technologies that can deliver high throughputs of light olefins in a cost efficient manner. Whereas steam cracking relies on non-selective thermal reactions of naphtha range hydrocarbons at very high temperatures, OTO exploits catalytic and micro-architectural properties of acidic molecular sieves under milder temperature conditions to produce high yields of ethylene and propylene from methanol.

Current understanding of the OTO reactions suggests a complex sequence in which three major steps can be identified: (1) an induction period leading to the formation of an active carbon pool (alkylaromatics), (2) alkylation-dealkylation reactions of these active intermediates leading to products, and (3) a gradual build-up of condensed ring aromatics. OTO is therefore a transient chemical transformation in which the catalyst is in a continuous state of change. The ability of the catalyst to maintain high olefin yields for prolonged periods of time relies on a delicate balance between the relative rates at which the above processes take place. The formation of coke-like molecules is of singular importance because their accumulation interferes with the desired reaction sequence in a number of ways. In particular, coke renders the carbon pool inactive, lowers the rates of diffusion of reactants and products, increases the potential for undesired secondary reactions and limits catalyst life.

Over the last two decades, many catalytic materials have been identified as being useful for carrying out the OTO reactions. Crystalline molecular sieves are the preferred catalysts today because they simultaneously address the acidity and morphological requirements for the reactions. Particularly preferred materials are eight-membered ring aluminosilicates, such as those having the chabazite (CHA) framework type, as well as silicoaluminophosphates of the CHA framework type, such as SAPO-34.

CHA framework type molecular sieves appear to be particularly suitable catalysts for the OTO reaction since they have cages that are sufficiently large to accommodate aromatic intermediates while still allowing the diffusional transport of reactants and products into and out of the crystals through regularly interconnected window apertures. By complementing such morphological characteristics with appropriate levels of acid strength and acid density, working catalysts are produced. Extensive research in this area indicates that increasing the silica to alumina molar ratio seems to be a key requirement in the use of CHA framework type aluminosilicates in OTO reactions.

There is therefore significant interest in developing synthesis routes for the production of CHA framework type aluminosilicates having a high silica to alumina ratio, typically in excess of 100:1, and in particular in developing synthesis routes that are simple, inexpensive and readily amenable to large scale commercial production.

Chabazite is a naturally-occurring zeolite with the approximate formula $Ca_6Al_{12}Si_{24}O_{72}$. Three synthetic forms of chabazite are described in "Zeolite Molecular Sieves", by D. W. Breck, published in 1973 by John Wiley & Sons, the disclosure of which is incorporated herein by reference. The three synthetic forms reported by Breck are Zeolite "K-G", described in J. Chem. Soc., p. 2822 (1956), Barrer et al; Zeolite D, described in British Patent No. 868,846 (1961); and Zeolite R, described in U.S. Pat. No. 3,030,181 (1962). Zeolite K-G has a silica:alumina mole ratio of 2.3:1 to 4.15:1, whereas zeolites D and R have silica:alumina mole ratios of 4.5:1 to 4.9:1 and 3.45:1 to 3.65:1, respectively, making these materials less than optimal as catalysts fro OTO reactions.

U.S. Pat. No. 4,544,538, incorporated herein by reference, describes the synthesis of another synthetic form of chabazite, SSZ-13, using N-alkyl-3-quinuclidinol, N,N,N-trialkyl-1-adamantylammonium cations and/or N,N,N-trialkyl-exoaminonorbornane as a directing agent in a conventional OH-medium. According to this patent, SSZ-13 typically has a silica to alumina molar ratio of 8 to 50, but it is stated that higher molar ratios can be obtained by varying the relative ratios of the reactants in the synthesis mixture and/or by treating the zeolite with chelating agents or acids to remove aluminum from the zeolite lattice. However, attempts to synthesize SSZ-13 in $OH^-$ media at silica to alumina molar ratios in excess of 100 have been unsuccessful and have produced ITQ-1 or SSZ-23, depending on the alkali metal cation present. Moreover, increasing the silica to alumina molar ratio of SSZ-13 by dealumination has met little or no success.

U.S. Pat. No. 6,709,644 describes a zeolite that is identified as SSZ-62 and has a CHA framework-type and a crystal size of 0.5 micron or less. SSZ-62 is said to have a silica to alumina molar ratio in excess of 10, such as in excess of 30, but the only synthesis example produces a material with a silica to alumina molar ratio of 22. Synthesis is effected in a hydroxyl medium in the presence of N,N,N-trimethyl-1-adamantammonium cation as the structure directing agent.

In a paper entitled "Templates in the transformation of zeolites to organozeolites. Cubic P conversions", ACS Symposium Series (1990), 437 (Novel Mater. Heterog. Catal.), 14 to 24, Zones et al. disclose that the treatment of low-silica zeolite P with a $RMe_3NI$ directing agent, where R is cyclohexyl, 2- or 3-methylcyclohexyl; 2-exo- or 2-endo-norbornyl, 2-bicyclo[3.2.1]octyl, 9-bicyclo[3.3.1]nonyl, or 1- or 2-adamantyl, leads to the crystallization of high-silica SSZ-13 containing the directing agent. However, the silica/alumina ratios of the SSZ-13 produced are reported to be in the range 11 to 13.

An all silica crystalline molecular sieve having the CHA framework type has been hydrothermally synthesized using N,N,N-trimethyladamantylammonium in hydroxide form as the structure-directing agent, but the synthesis requires the presence of concentrated hydrofluoric acid. See Diaz-Cabanas, M-J, Barrett, P. A., and Camblor, M. A. "Synthesis and Structure of Pure SiO$_2$ Chabazite: the SiO$_2$ Polymorph with the Lowest Framework Density", Chem. Commun. 1881 (1998).

More recently, an aluminosilicate with the CHA framework type and having a silica to alumina molar ratio in excess of 100, such as from 150 to 2000, has been synthesized, again in presence of concentrated hydrofluoric acid. See U.S. Patent Application Publication No. 2003/0176751, published Sep. 18, 2003 and incorporated herein by reference. The directing agent employed is selected from N-alkyl-3-quinuclidinol cations, N,N,N-tri-alkyl-1-adamantammonium cations and N,N,N-trialkyl-exoaminonorbornane cations.

Synthesis processes that involve working with corrosive materials, such as concentrated hydrofluoric acid, present significant practical problems especially on a commercial scale. Moreover, current methods of synthesizing silicates and high silica aluminosilicates having the CHA framework type require the use of expensive directing agents and/or reaction mixtures with a low water content and hence high viscosity. Both of these features can provide further obstacles to process scale-up.

There is, therefore, a need for a process for synthesizing crystalline silicates and high silica aluminosilicates including a CHA framework type molecular sieve in which the process employs a reaction mixture that is substantially free of added hydrofluoric acid. The desired process would use an inexpensive structure directing agent and/or a high water content. The desired process would ideally be applicable to not only silicates and aluminosilicates, but also to the synthesis of CHA framework type molecular sieves in which part of all of the silicon is replaced by another tetravalent element, such as tin, titanium, germanium or a combination thereof, and part or all of any aluminum is replaced by another trivalent element, such as boron, iron, indium, gallium or a combination thereof. There is also a need for a method for making a crystalline product that is not necessarily a pure phase CHA material, but can also include stacking faults and/or include an intergrowth of a CHA material with another framework type molecular sieve, such as an AEI framework type material.

U.S. Pat. No. 7,094,389 describes a crystalline material substantially free of framework phosphorus and comprising a CHA framework type molecular sieve with stacking faults or at least one intergrown phase of a CHA framework type molecular sieve and an AEI framework type molecular sieve, wherein said material, in its calcined, anhydrous form, has a composition involving the molar relationship: $(n)X_2O_3:YO_2$, wherein X is a trivalent element; Y is a tetravalent element; and n is from 0 to about 0.5. The material exhibits activity and selectivity in the conversion of methanol to lower olefins, especially ethylene and propylene.

SUMMARY

In one aspect, the invention resides in a method of synthesizing a crystalline material comprising a CHA framework type molecular sieve and having a composition involving the molar relationship:

$(n)X_2O_3:YO_2$ wherein X is a trivalent element; Y is a tetravalent element; and n is from 0 to less than 0.01, such as from about 0.0005 to about 0.007, the method comprising:

(a) preparing a reaction mixture capable of forming the material, the reaction mixture comprising a (i) source of water, (ii) a source of an oxide of a tetravalent element Y and optionally a source of an oxide of a trivalent element X, wherein the reaction mixture is substantially free of fluoride ions added as HF, and (iii) an organic directing agent for directing the formation of a CHA framework type molecular sieve and having the formula:

$[R^1R^2R^3N\text{—}R^4]^+Q^-$ wherein $R^1$ and $R^2$ are independently selected from hydrocarbyl alkyl groups and hydroxy-substituted hydrocarbyl groups having from 1 to 3 carbon atoms, provided that $R^1$ and $R^2$ may be joined to form a nitrogen-containing heterocyclic structure, $R^3$ is an alkyl group having 2 to 4 carbon atoms and $R^4$ is selected from a 4- to 8-membered cycloalkyl group, optionally substituted by 1 to 3 alkyl groups each having from 1 to 3 carbon atoms, and a 4- to 8-membered heterocyclic group having from 1 to 3 heteroatoms, the heterocyclic group being optionally substituted by 1 to 3 alkyl groups each having from 1 to 3 carbon atoms and the or each heteroatom in the heterocyclic group being selected from the group consisting of O, N, and S, or $R^3$ and $R^4$ are hydrocarbyl groups having from 1 to 3 carbon atoms joined to form a nitrogen-containing heterocyclic structure; and $Q^-$ is an anion;

(b) maintaining the reaction mixture under conditions sufficient to form crystals of the crystalline material; and (c) recovering the crystalline material from (b).

In an embodiment, the reaction mixture is substantially free of all fluoride ions.

While not required the reaction mixture can have an H$_2$O:YO$_2$ molar ratio of about 10 to about 40, and preferably from greater than 20 to about 30.

In an embodiment, the crystalline material is substantially free of framework phosphorus.

In one embodiment, $R^1$ and $R^2$ are independently selected from a methyl group and an ethyl group. Conveniently, $R^3$ is an ethyl group and $R^4$ is a cyclohexyl group. Preferably, $[R^1R^2R^3N\text{—}R^4]^+$ is selected from N,N,N-dimethylethylcyclohexylammonium, N,N,N-methyldiethylcyclohexylammonium, and N,N,N-triethylcyclohexylammonium.

In another embodiment, $R^1$ and $R^2$ are joined to form a substituted or unsubstituted five-membered nitrogen-containing heterocyclic ring. Conveniently, $R^3$ and $R^4$ are hydrocarbyl groups joined to form a substituted or unsubstituted six-membered nitrogen-containing heterocyclic ring. Preferably, $[R^1R^2R^3N\text{—}R^4]^+$ is 2,7-dimethyl-1-azonium[5,4]decane.

In an embodiment, the reaction mixture further comprises (iv) a second organic directing agent for directing the formation of an AEI framework type molecular sieve. Preferably, the second organic directing agent comprises a monocyclic amine or ammonium compound, such as a substituted piperidine or piperidinium compound, for example an N,N-diethyl-2,6-dimethylpiperidinium compound In an embodiment, the reaction mixture comprises from about 0.01 ppm by weight to about 10,000 ppm by weight, such as from about 100 ppm by weight to about 5,000 ppm by weight of seeds based on the weight of the reaction mixture. Conveniently, said seeds comprise a crystalline material having one or more of an AEI, LEV, CHA, ERI, AFX or OFF framework-type.

The conditions in (b) can include, for example, a temperature of between about 120° C. and about 220° C.

In a further aspect, the invention resides in a method of synthesizing a crystalline material comprising a CHA framework type molecular sieve and having a composition involving the molar relationship:

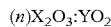
$(n)X_2O_3:YO_2$ wherein X is a trivalent element; Y is a tetravalent element; and n is from 0 to less than 0.01, such as from about 0.0005 to about 0.007, the method comprising:

(a) preparing a reaction mixture capable of forming the material, the reaction mixture comprising a source of water, a source of an oxide of a tetravalent element Y and optionally a source of an oxide of a trivalent element X, wherein the reaction mixture is substantially free of fluoride ions added as HF and has an $H_2O:YO_2$ molar ratio of greater than 20;

(b) maintaining the reaction mixture under conditions sufficient to form crystals of said crystalline material; and (c) recovering the crystalline material from (b).

In yet a further aspect, the invention resides in a method of synthesizing a crystalline material comprising a CHA framework type molecular sieve which is free of stacking faults and/or any intergrown phase with an AEI framework type molecular sieve, the crystalline material having a composition involving the molar relationship:

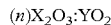
$(n)X_2O_3:YO_2$ wherein X is a trivalent element; Y is a tetravalent element; and n is from 0 to less than 0.01, such as from about 0.0005 to about 0.007, the method comprising:

(a) preparing a reaction mixture capable of forming the material, the reaction mixture comprising a source of water, a source of an oxide of a tetravalent element Y and optionally a source of an oxide of a trivalent element X, wherein the reaction mixture is substantially free of fluoride ions added as HF;

(b) maintaining the reaction mixture under conditions sufficient to form crystals of said crystalline material; and (c) recovering the crystalline material from (b).

In yet a further aspect, the invention resides in a process for producing olefins comprising contacting an organic oxygenate compound under oxygenate conversion conditions with a catalyst comprising a porous crystalline material produced by the method described herein. In an embodiment, the olefins comprise ethylene and/or propylene. The ethylene and/or propylene can be polymerized to form polymers and copolymers comprising polyethylene and/or polypropylene.

BRIEF DESCRIPTION OF THE DRAWINGS

FIGS. 1(a) to 1(e) are X-ray diffraction patterns of the as-synthesized products of Runs 1 to 5 respectively of Example 2.

FIGS. 2(a) and 2(b) are X-ray diffraction patterns of the as-synthesized products of Example 3 after 2 days and 3 days, respectively.

DETAILED DESCRIPTION OF THE EMBODIMENTS

Figures 3A, 3B, 3C, 3D, 3E, 3F, 3G:
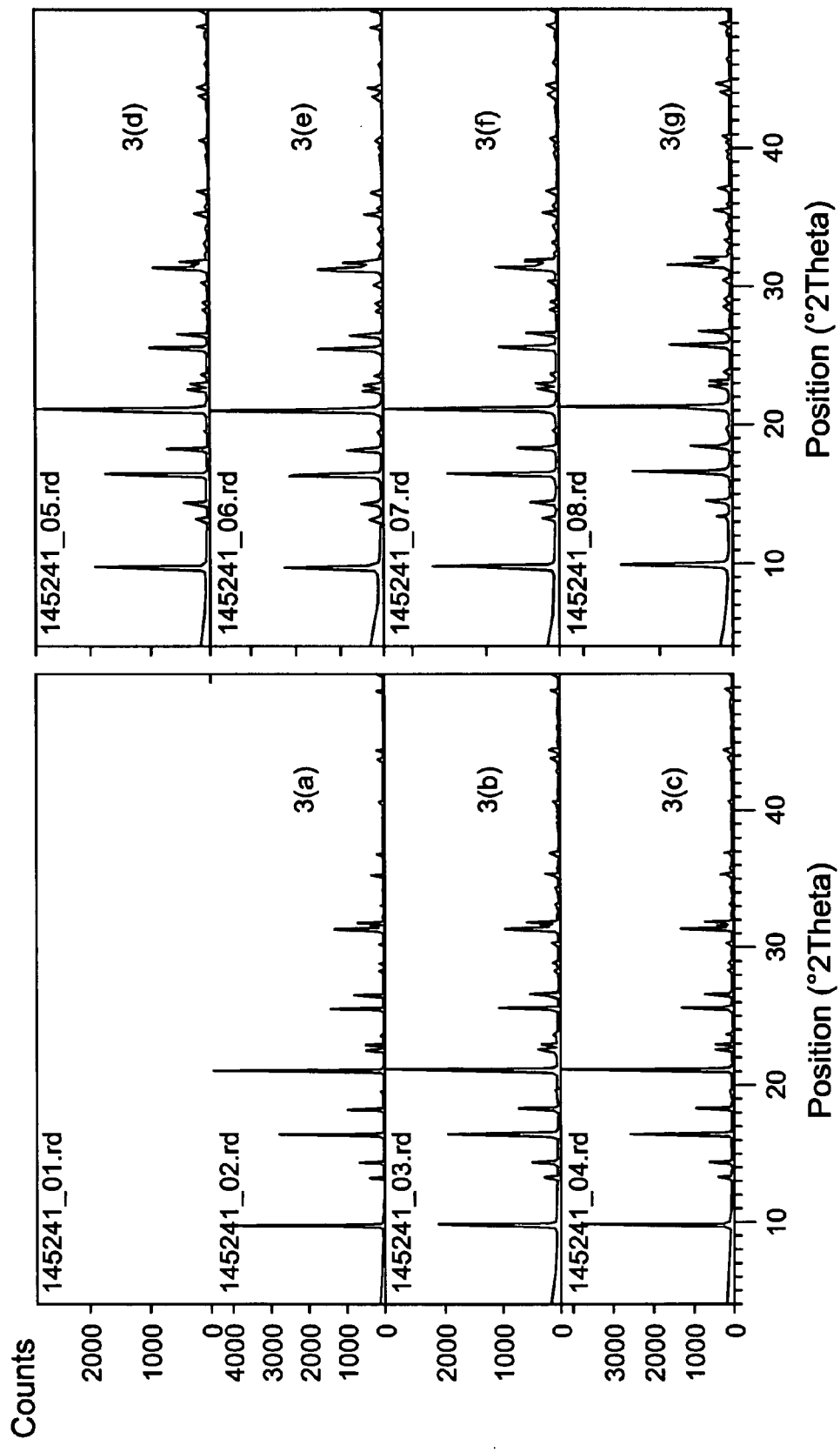
FIGS. 3(a) to 3(g) are X-ray diffraction patterns of the as-synthesized products of Runs 1 to 7 respectively of Example 4.

In an embodiment, the invention relates to a method of synthesizing a crystalline material, in particular a high silica zeolite, comprising a chabazite (CHA) framework type molecular sieve. The synthesis method of the invention employs a reaction mixture that is substantially free of added hydrofluoric acid and that uses an inexpensive structure directing agent and/or a high water content. In addition, the invention relates to the use of the resultant molecular sieve, particularly as a catalyst in a process for the conversion of oxygenates, particularly methanol, to olefins, particularly ethylene and propylene.

Molecular sieves are classified by the Structure Commission of the International Zeolite Association according to the rules of the IUPAC Commission on Zeolite Nomenclature. According to this classification, framework-type zeolites and other crystalline microporous molecular sieves, for which a structure has been established, are assigned a three letter code and are described in the *Atlas of Zeolite Framework Types*, 5th edition, Elsevier, London, England (2001). Chabazite is one of the molecular sieves for which a structure has been established and materials of this framework-type are designated as CHA.

In its calcined form, a high silica CHA-type molecular sieve, such as can be produced by the method of the present invention has an X-ray diffraction pattern having the characteristic lines shown in Table 1 below:

TABLE 1

| d(A) | Relative Intensities 100 I/Io |
|---|---|
| 9.36-8.98 | 80-100 |
| 6.86-6.66 | 20-60 |
| 6.33-6.15 | 0-10 |
| 5.51-5.38 | 5-40 |
| 4.97-4.86 | 5-50 |
| 4.63-4.54 | 0-10 |
| 4.28-4.20 | 20-60 |
| 3.94-3.87 | 0-10 |
| 3.83-3.76 | 0-10 |
| 3.54-3.49 | 5-40 |
| 3.41-3.36 | 5-40 |
| 3.14-3.10 | 0-10 |
| 2.889-2.853 | 5-50 |
| 2.850-2.815 | 5-40 |
| 2.650-2.620 | 0-10 |
| 2.570-2.542 | 0-10 |
| 2.467-2.441 | 0-10 |
| 2.244-2.223 | 0-10 |
| 2.088-2.070 | 0-10 |
| 2.059-2.041 | 0-10 |
| 1.883-1.869 | 0-10 |
| 1.842-1.828 | 0-10 |

These X-ray diffraction data were collected with a Philips powder X-Ray Diffractometer, equipped with a scintillation detector with graphite monochromator, using copper K-alpha radiation. The diffraction data were recorded by step-scanning at 0.02 degrees of two-theta, where theta is the Bragg angle, and a counting time of 1 second for each step. The interplanar spacing, d's, were calculated in Angstrom units, and the relative intensities of the lines, (where $I/I_o$ is one-hundredth of the intensity of the strongest line), above background were determined by integrating the peak intensities. It should be understood that diffraction data listed for this sample as single lines may consist of multiple overlapping lines which under certain conditions, such as differences in crystallographic changes, may appear as resolved or partially resolved lines. Typically, crystallographic changes can include minor changes in unit cell parameters and/or a change in crystal symmetry, without a change in the framework atom connectivities. These minor effects, including changes in relative intensities, can also occur as a result of differences in cation content, framework composition, nature and degree of pore filling, crystal size and shape, preferred orientation and thermal and/or hydrothermal history.

CHA framework type molecular sieves and other regular crystalline solids are built from structurally invariant building units, called Periodic Building Units, and are periodically ordered in three dimensions. Structurally disordered materials are also known and show periodic ordering in dimensions less than three, i.e. in two, one or zero dimensions. This phenomenon is called stacking disorder of structurally invariant Periodic Building Units. Crystal structures built from Periodic Building Units are called end-member structures if periodic ordering is achieved in all three dimensions. Disordered structures are those where the stacking sequence of the Periodic Building Units deviates from periodic ordering up to statistical stacking sequences.

Intergrown molecular sieve phases are disordered planar intergrowths of molecular sieve frameworks. Reference is directed to the "Catalog of Disordered Zeolite Structures", 2000 Edition, published by the Structure Commission of the International Zeolite Association and to the "Collection of Simulated XRD Powder Patterns for Zeolites", M. M. J. Treacy and J. B. Higgins, 2001 Edition, published on behalf of the Structure Commission of the International Zeolite Association for a detailed explanation on intergrown molecular sieve phases.

In the case of a regular CHA framework type molecular sieve, the Periodic Building Unit is a double six ring layer. There are two types of layers "a" and "b", which are topologically identical except "b" is the mirror image of "a". When layers of the same type stack on top of one another, i.e. aaaaaaaa or bbbbbbbb, the framework type CHA is generated. When layers "a" and "b" alternate, ie, abababab, a different framework type, AEI, is generated. Intergrown CHA/AEI molecular sieves comprise regions of CHA framework type sequences and regions of AEI framework type sequences. Each change from a CHA to an AEI framework type sequence results in a stacking fault. In addition, stacking faults can occur in a pure CHA phase material when a sequence of one mirror image layers intersects a sequence of the opposite mirror image layers, such as for example in aaaaaabbbbbbb.

AEI framework type molecular sieves exhibit a different X-ray diffraction pattern from CHA framework type materials. Thus analysis of intergrown molecular sieves, such as AEI/CHA intergrowths, can be effected by X-ray diffraction and in particular by comparing the observed patterns with calculated patterns generated using algorithms to simulate the effects of stacking disorder. DIFFaX is a computer program based on a mathematical model for calculating intensities from crystals containing planar faults (see M. M. J. Treacy et al., Proceedings of the Royal Chemical Society, London, A [1991], Vol. 433, pp. 499-520). DIFFaX is the simulation program selected by and available from the International Zeolite Association to simulate the XRD powder patterns for randomly intergrown phases of zeolites (see "Collection of Simulated XRD Powder Patterns for Zeolites" by M. M. J. Treacy and J. B. Higgins, 2001, Fourth Edition, published on behalf of the Structure Commission of the International Zeolite Association). It has also been used to theoretically study intergrown phases of AEI, CHA and KFI, as reported by K. P. Lillerud et al. in "Studies in Surface Science and Catalysis", 1994, Vol. 84, pp. 543-550.

In an embodiment, the invention relates to a process for making crystalline materials comprising a CHA framework type molecular sieve, either alone as a pure phase material, or in the presence of stacking faults or including at least one intergrown phase of a CHA framework type molecular sieve with a different phase, such as an AEI framework type molecular sieve. In its calcined and anhydrous form, the material has a composition involving the following molar relationship:

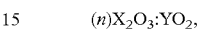
$(n)X_2O_3:YO_2$, wherein X (if present) is a trivalent element, such as aluminum, boron, iron, indium, gallium or a combination thereof, typically aluminum; Y is a tetravalent element, such as silicon, tin, titanium, germanium or a combination thereof, typically silicon; and n is from 0 to less than 0.01, such as from about 0.0005 to about 0.007. Preferably, the material is substantially free of framework phosphorus.

In its as-synthesized form, the crystalline material has the molar relationship:

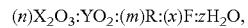
$(n)X_2O_3:YO_2:(m)R:(x)F:zH_2O$, wherein X, Y and n are as defined in the preceding paragraph; R is at least one organic directing agent; m ranges from about 0.01 to about 2, such as from about 0.1 to about 1; z ranges from about 0.5 to about 100, such as from about 2 to about 20; and x ranges from about 0 to about 2, such as from about 0 to about 1. Preferably, x is zero. The R component and, if present, the F component are associated with the material as a result of their presence during crystallization and can be at least partly removed by post-crystallization methods hereinafter more particularly described. Typically, the as-synthesized CHA framework-type crystalline material of the present invention contains only low levels of alkali metal, generally such that the combined amount of any potassium and sodium is less than 50% of the $X_2O_3$ on a molar basis. For this reason, after removal of the organic directing agent (R), the material generally exhibits catalytic activity without a preliminary ion-exchange step to remove alkali metal cations.

To the extent desired and depending on the $X_2O_3/YO_2$ molar ratio of the material, any cations in the as-synthesized CHA framework-type material can be replaced in accordance with conventional techniques (ie., techniques known in the art), at least in part, by ion exchange with other cations. Preferred replacing cations include metal ions, hydrogen ions, hydrogen precursor, e.g., ammonium ions, and mixtures thereof. Particularly preferred cations are those which tailor the catalytic activity for certain hydrocarbon conversion reactions. These include hydrogen, rare earth metals and metals of Groups IIA, IIIA, IVA, VA, IB, IIB, IIIB, IVB, VB, VIIB, VIIB and VIII of the Periodic Table of the Elements.

The crystalline material can be prepared from a reaction mixture containing a source of water, a source of an oxide of the tetravalent element Y, optionally a source of an oxide of the trivalent element X, and at least one organic directing agent (R) as described below, wherein the reaction mixture is substantially free of fluoride ions (e.g., those added thereto as HF). Preferably, the reaction mixture is substantially free of all fluoride ions, although in some cases fluoride ions may be present provided they are added as neutral fluoride salts, for example of the directing agent (R). Useful and typical ranges for the composition, in terms of mole ratios of oxides, of the reaction mixture are given in the following table:

| Reactants | Useful | Typical |
|---|---|---|
| $H_2O/YO_2$ | 0.1 to 40 | 5 to 30 |
| Fluoride/$YO_2$ | 0 to 2 | 0 to 1 |
| R/$YO_2$ | 0.01 to 2 | 0.1 to 1 |
| $X_2O_3/YO_2$ | 0 to 0.01 | 0.0005 to 0.007 |

Depending on the organic directing agent R, the synthesis process can be conducted under high dilution, typically at an $H_2O:YO_2$ molar ratio of about 10 to about 40, and preferably from greater than 20 to about 30. At such high dilutions the viscosity of reaction mixture, and hence its resistance to the stirring normally required in large scale syntheses, is reduced.

Where the tetravalent element Y is silicon, suitable sources of silicon include silicates, e.g., tetraalkyl orthosilicates, fumed silica, such as Aerosil (available from Degussa), and aqueous colloidal suspensions of silica, for example that sold by E.I. du Pont de Nemours under the tradename Ludox. Where the trivalent element X is aluminum, suitable sources of aluminum include aluminum salts, especially water-soluble salts, such as aluminum nitrate, as well as hydrated aluminum oxides, such as boehmite and pseudoboehmite. Where the halide is fluoride, suitable sources of fluoride include hydrogen fluoride, although more benign sources of fluoride such as alkali metal fluorides and fluoride salts of the organic directing agent are preferred.

Suitable organic directing agents R for directing the synthesis of a CHA framework-type material include adamantammonium compounds, such as N,N,N-trimethyl-1-adamantammonium compounds, N,N,N-trimethyl-2-adamantammonium compounds, and N,N,N-trimethylcyclohexylammonium compounds, N,N-dimethyl-3,3-dimethylpiperidinium compounds, N,N-methylethyl-3,3-dimethylpiperidinium compounds, N,N-dimethyl-2-methylpiperidinium compounds, 1,3,3,6,6-pentamethyl-6-azonio-bicyclo(3.2.1)octane compounds, N,N-dimethylcyclohexylamine, and the bi- and tri-cyclic nitrogen containing organic compounds cited in (1)*Zeolites and Related Microporous Materials*: State of the Art 1994, Studies of Surface Science and Catalysis, Vol. 84, p 29-36; in (2) *Novel Materials in Heterogeneous Catalysis* (ed. Terry K. Baker & Larry L. Murrell), Chapter 2, p 14-24, May 1990, in (3) J. Am. Chem. Soc., 2000, 122, p 263-273 and (4) in U.S. Pat. Nos. 4,544,538 and 6,709,644. Suitable compounds include hydroxides and salts, such as neutral halides, for example chlorides and fluorides.

In another embodiment, the organic directing agent R used herein to direct the formation of a CHA framework type molecular sieve is a cyclic ammonium compound having the formula:

[$R^1R^2R^3N$—$R^4$]$^+Q^-$ wherein $R^1$ and $R^2$ are independently selected from hydrocarbyl groups and hydroxy-substituted hydrocarbyl groups having from 1 to 3 carbon atoms, provided that $R^1$ and $R^2$ may be joined to form a nitrogen-containing heterocyclic structure, $R^3$ is an alkyl group having 2 to 4 carbon atoms and $R^4$ is selected from a 4- to 8-membered cycloalkyl group, optionally substituted by 1 to 3 alkyl groups each having from 1 to 3 carbon atoms; and a 4- to 8-membered heterocyclic group having from 1 to 3 heteroatoms, the heterocyclic group being optionally substituted by 1 to 3 alkyl groups each having from 1 to 3 carbon atoms and the or each heteroatom in the heterocyclic group being selected from the group consisting of O, N, and S, or $R^3$ and $R^4$ are hydrocarbyl groups having from 1 to 3 carbon atoms joined to form a nitrogen-containing heterocyclic structure; and $Q^-$ is an anion, such as hydroxide or halide.

In one embodiment, $R^4$ is a cyclohexyl group, $R^1$ and $R^2$ are independently selected from a methyl group and an ethyl group and $R^3$ is an ethyl group. In this embodiment, preferred [$R^1R^2R^3N$—$R^4$]$^+$ cations include N,N,N-dimethylethylcyclohexylammonium (DMECHA):

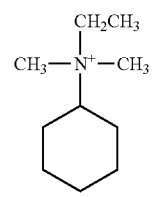

N,N,N-methyldiethylcyclohexylammonium (MDECHA):

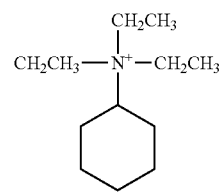

and N,N,N-triethylcyclohexylammonium (TECHA):

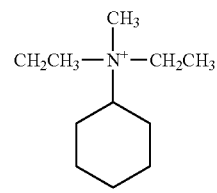

In another embodiment, $R^1$ and $R^2$ are joined to form a substituted or unsubstituted five-membered nitrogen-containing heterocyclic ring. Conveniently, $R^3$ and $R^4$ are hydrocarbyl groups joined to form a substituted or unsubstituted six-membered nitrogen-containing heterocyclic ring. In this embodiment, a preferred [$R^1R^2R^3N$—$R^4$]$^+$ cation includes 2,7-dimethyl-1-azonium[5,4]decane (DM27AD):

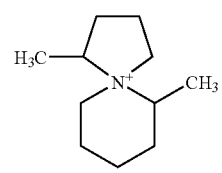

In addition to the organic directing agent for directing the formation of a CHA framework-type molecular sieve, the reaction mixture can also comprise a further organic directing agent for directing the formation of an AEI framework type molecular sieve. In this case, the resultant crystalline material will tend to contain either stacking faults or at least one intergrown phase of a CHA framework type molecular sieve and an AEI framework type molecular sieve. Conveniently, the further organic directing agent comprises a monocyclic amine or ammonium compound, such as a substituted piperidine or piperidinium compound, for example a tetraalkylpiperidinium compound, typically an N,N-diethyl-2,6-dimethylpiperidinium compound.

While not required, the reaction mixture can also contain seeds to facilitate the crystallization process. The amount of seeds employed is not critical. When seeds are used, the reaction mixture generally comprises from about 0.1 ppm by weight to about 10,000 ppm by weight, such as from about 100 ppm by weight to about 5,000 by weight, of seeds based on the weight of the reaction mixture. Conveniently, the seeds comprise a crystalline material having an AEI, LEV, CHA, ERI, AFX or OFF framework-type molecular sieve. The seeds may be added to the reaction mixture as a colloidal suspension in a liquid medium, such as water. The production of colloidal seed suspensions and their use in the synthesis of molecular sieves are disclosed in, for example, International Publication Nos. WO 00/06493 and WO 00/06494 published on Feb. 10, 2000 and incorporated herein by reference.

Conveniently, the reaction mixture has a pH of about 4 to about 14, such as about 5 to about 13, for example about 6 to about 12.

Crystallization can be carried out at either static or stirred conditions in a suitable reactor vessel, such as for example, polypropylene jars or Teflon®-lined or stainless steel autoclaves, at a temperature of about 120° C. to about 220° C., such as about 140° C. to about 200° C., for a time sufficient for crystallization to occur. Formation of the crystalline product can take anywhere from around 30 minutes up to as much as 2 weeks, such as from about 45 minutes to about 240 hours, for example from about 1.0 to about 120 hours. The duration depends on the temperature employed, with higher temperatures typically requiring shorter hydrothermal treatments.

Typically, the crystalline product is formed in solution and can be recovered by conventional methods, such as by centrifugation or filtration. The separated product can also be washed, recovered by centrifugation or filtration and dried. The resultant product is found to comprise particles with an average crystal size below 4 microns, such as below 2 microns and typically about 1 micron.

As a result of the crystallization process, the recovered crystalline product contains within its pores at least a portion of the organic directing agent used in the synthesis. In a preferred embodiment, activation is performed in such a manner that the organic directing agent is removed from the molecular sieve, leaving active catalytic sites within the microporous channels of the molecular sieve open for contact with a feedstock. The activation process is typically accomplished by calcining, which involves heating the molecular sieve comprising the template at a temperature of from about 200° C. to about 800° C. in the presence of an oxygen-containing gas. In some cases, it may be desirable to heat the molecular sieve in an environment having a low or zero oxygen concentration. This type of process can be used for partial or complete removal of the organic directing agent from the intracrystalline pore system. In other cases, particularly with smaller organic directing agents, complete or partial removal from the sieve can be accomplished by conventional desorption processes.

Once the CHA framework-type containing material has been synthesized, it can be formulated into a catalyst composition by combination with other materials, such as binders and/or matrix materials, that provide additional hardness or catalytic activity to the finished catalyst. Conventional methods can be used.

Various inert or catalytically active materials can be added to the CHA framework-type containing materials. These added materials include compositions such as kaolin and other clays, various forms of rare earth metals, other non-zeolite catalyst components, zeolite catalyst components, alumina or alumina sol, titania, zirconia, quartz, silica or silica sol, and mixtures thereof. These components are generally effective in reducing overall catalyst cost, acting as a thermal sink to assist in heat shielding the catalyst during regeneration, densifying the catalyst, and increasing catalyst strength. When blended with such components, the amount of molecular sieve, e.g., zeolitic material, contained in the final catalyst product ranges from 10 to 90 weight percent of the total catalyst, preferably 20 to 70 weight percent of the total catalyst.

The crystalline material can be used to dry gases and liquids; for selective molecular separation based on size and polar properties; as an ion-exchanger; as a chemical carrier; in gas chromatography; and as a catalyst in catalytic conversion reactions. Examples of suitable catalytic uses of the crystalline material include (a) hydrocracking of heavy petroleum residual feedstocks, cyclic stocks and other hydrocrackate charge stocks, normally in the presence of a hydrogenation component selected from Groups 6 and 8 to 10 of the Periodic Table of Elements; (b) catalytic dewaxing, including isomerization dewaxing, to selectively remove straight chain paraffins from hydrocarbon feedstocks typically boiling above 177° C., including raffinates and lubricating oil basestocks; (c) catalytic cracking of hydrocarbon feedstocks, such as naphthas, gas oils and residual oils, normally in the presence of a large pore cracking catalyst, such as zeolite Y; (d) oligomerization of straight and branched chain olefins having from about 2 to 21, preferably 2 to 5 carbon atoms, to produce medium to heavy olefins which are useful for both fuels, i.e., gasoline or a gasoline blending stock, and chemicals; (e) isomerization of olefins, particularly olefins having 4 to 6 carbon atoms, and especially normal butene to produce iso-olefins; (f) upgrading of lower alkanes, such as methane, to higher hydrocarbons, such as ethylene and benzene; (g) disproportionation of alkylaromatic hydrocarbons, such as toluene, to produce dialkylaromatic hydrocarbons, such as xylenes; (h) alkylation of aromatic hydrocarbons, such as benzene, with olefins, such as ethylene and propylene, to produce ethylbenzene and cumene; (i) isomerization of dialkylaromatic hydrocarbons, such as xylenes, (j) catalytic reduction of nitrogen oxides and (k) synthesis of monoalkylamines and dialkylamines.

In particular, the crystalline material produced by the method of the invention is useful in the catalytic conversion of oxygenates to one or more olefins, particularly ethylene and propylene. As used herein, the term "oxygenates" includes, for example, aliphatic alcohols, ethers, carbonyl compounds (aldehydes, ketones, carboxylic acids, carbonates, and the like), and also compounds containing hetero-atoms, such as, halides, mercaptans, sulfides, amines, and mixtures thereof. The aliphatic moiety generally contains from about 1 to about 10 carbon atoms, such as from about 1 to about 4 carbon atoms.

Representative oxygenates include lower straight chain or branched aliphatic alcohols, their unsaturated counterparts, and their nitrogen, halogen and sulfur analogues. Examples of suitable oxygenate compounds include methanol; ethanol; n-propanol; isopropanol; $C_4$-$C_{10}$ alcohols; methyl ethyl ether; dimethyl ether; diethyl ether; di-isopropyl ether; methyl mercaptan; methyl sulfide; methyl amine; ethyl mercaptan; di-ethyl sulfide; di-ethyl amine; ethyl chloride; formaldehyde; di-methyl carbonate; di-methyl ketone; acetic acid; n-alkyl amines, n-alkyl halides, n-alkyl sulfides having n-alkyl groups of comprising the range of from about 3 to about 10 carbon atoms; and mixtures thereof. Particularly suitable oxygenate compounds are methanol, dimethyl ether, or mixtures thereof, most preferably methanol. In addition to oxygenates, the total charge of feed to the reaction zone can contain other species, such as diluents.

In an oxygenate conversion process, a feedstock comprising an oxygenate, optionally with one or more diluents, is contacted in the vapor phase in a reaction zone with a catalytically effective amount of a catalyst comprising the molecular sieve of the present invention under catalytic conversion conditions so as to produce the desired olefins. Alternatively, the process may be carried out in a liquid or a mixed vapor/liquid phase. When the process is carried out in the liquid phase or a mixed vapor/liquid phase, different conversion rates and selectivities of feedstock-to-product may result depending upon the catalyst and the reaction conditions.

When present, the diluent(s) is generally non-reactive to the feedstock or molecular sieve catalyst composition and is typically used to reduce the concentration of the oxygenate in the feedstock. Non-limiting examples of suitable diluents include helium, argon, nitrogen, carbon monoxide, carbon dioxide, water, essentially non-reactive paraffins (especially alkanes such as methane, ethane, and propane), essentially non-reactive aromatic compounds, and mixtures thereof. The most preferred diluents are water and nitrogen, with water being particularly preferred. Diluent(s) may comprise from about 1 mol % to about 99 mol % of the total feed mixture.

The temperature employed in the oxygenate conversion process may vary over a wide range, such as from about 200° C. to about 1000° C., for example from about 250° C. to about 800° C., including from about 250° C. to about 750° C., conveniently from about 300° C. to about 650° C., typically from about 350° C. to about 600° C. and particularly from about 400° C. to about 600° C.

Light olefin products will form, although not necessarily in optimum amounts, at a wide range of pressures, including, for example, autogenous pressures and pressures in the range of from about 0.1 kPa to about 10 MPa. For example, the pressure can be in the range of from about 7 kPa to about 5 MPa, such as in the range of from about 50 kPa to about 1 MPa. The foregoing pressures are exclusive of diluent, if any is present, and refer to the partial pressure of the feedstock as it relates to oxygenate compounds and/or mixtures thereof. Lower and upper extremes of pressure might in some cases adversely affect selectivity, conversion, coking rate, and/or reaction rate; however, light olefins such as ethylene still may form.

The process should be continued for a period of time sufficient to produce the desired olefin products. The reaction time may vary from tenths of seconds to a number of hours. The reaction time largely depends on the reaction temperature, the pressure, the catalyst selected, the weight hourly space velocity, the phase (liquid or vapor) and the selected process design characteristics.

A wide range of weight hourly space velocities (WHSV) for the feedstock will function in the present process. WHSV is defined as weight of feed (excluding diluent) per hour per weight of a total reaction volume of molecular sieve catalyst (excluding inerts and/or fillers). The WHSV generally should be in the range of from about 0.01 $hr^{-1}$ to about 500 $hr^{-1}$, such as in the range of from about 0.5 $hr^{-1}$ to about 300 $hr^{-1}$, for example in the range of from about 0.1 $hr^{-1}$ to about 200 $hr^{-1}$.

A practical embodiment of a reactor system for the oxygenate conversion process is a circulating fluid bed reactor with continuous regeneration, similar to a modern fluid catalytic cracker. Fixed beds can be used for the process, but since oxygenate to olefin conversion is a highly exothermic process, a fixed bed process would generally involve several stages with intercoolers or other cooling devices. The reaction also results in a high pressure drop due to the production of low pressure, low density gas.

Since the catalyst is typically regenerated and reused, the reactor should allow easy removal of at least a portion of the catalyst to a regenerator, where the catalyst is subjected to a regeneration medium, such as a gas comprising oxygen, for example air, to burn off coke from the catalyst, which restores the catalyst activity. The conditions of temperature, oxygen partial pressure, and residence time in the regenerator should be selected to achieve a coke content on regenerated catalyst of less than about 0.5 wt %. At least a portion of the regenerated catalyst should be returned to the reactor.

In one embodiment, the catalyst is pretreated with dimethyl ether, a $C_2$-$C_4$ aldehyde composition and/or a $C_4$-$C_7$ olefin composition to form an integrated hydrocarbon co-catalyst within the porous framework of the CHA framework-type molecular sieve prior to the catalyst being used to convert oxygenate to olefins. Desirably, the pretreatment is conducted at a temperature of at least 10° C., such as at least 25° C., for example at least 50° C., higher than the temperature used for the oxygenate reaction zone and is arranged to produce at least 0.1 wt %, such as at least 1 wt %, for example at least about 5 wt % of the integrated hydrocarbon co-catalyst, based on total weight of the molecular sieve. Such preliminary treating to increase the carbon content of the molecular sieve is known as "pre-pooling" and is further described in U.S. application Ser. Nos. 10/712,668, 10/712,952 and 10/712,953 all of which were filed Nov. 12, 2003 and are incorporated herein by reference.

The invention will now be more particularly described with reference to the following Examples and the accompanying drawings.

In the Examples, X-ray Powder Diffractograms were recorded on a Siemens D500 diffractometer with voltage of 40 kV and current of 30 mA, using a Cu target and Ni-filter (Λ=0.154 nm). Elemental analysis of Al, Si, and P was performed using the Inductively Coupled Plasma (ICP) spectroscopy.

EXAMPLE 1

Synthesis of
N,N,N-dimethylethylcyclohexylammonium
hydroxide (DMECHA Hydroxide)

45.0 g ethylbromide was added to a mixture of 50.0 g N,N-dimethylcyclohexylamine and 100 g ethanol. The solution was sealed in a polypropylene bottle and was placed in a 50° C. oven overnight. The ethanol was evaporated at 50° C. with the aid of flowing nitrogen, and to the remaining thick liquid (with some crystals) was added 50 g deionized water. A clear solution of the bromide salt was thus obtained. The aqueous solution was ion-exchanged with Bio Rad AG® 1-X8 Resin (OH— exchanger) three times (3×60 g) until $AgNO_3$ test showed only trace amount of silver bromide. The hydroxide solution was finally concentrated to a desired concentration by evaporating water on a Rotavap®.

EXAMPLE 2

Synthesis of High Silica Chabazite Using DMECHA Hydroxide

The following ingredients were mixed, in sequence, and blended into a uniform gel using a microhomogenizer (Tissue Tearor Model 98730 available from Biospec Products, Inc, USA): 50 wt % NaOH solution, a 42.7 wt % aqueous solution of N,N,N-dimethylethylcyclohexylammonium hydroxide (DMECHAOH) produced in Example 1, deionized water if necessary, and Hi-Sil® 233 (PPG Industries, USA). The Hi-Sil contained 0.53 wt % Na, 0.01 wt % K, 0.42 wt % alumina, and 82.2 wt % silica (Si/Al ratio of the material is 164). The ingredients were mixed in various molar ratios as shown in the Table 2 below. Finally 200 ppm colloidal seeds (having LEV structure) were added to each synthesis mixture and the mixture was sealed in a Teflon® lined Parr bomb with no aging and heated in an oven at a preset temperature, either statically or tumbled at 40 rpm. After a certain time the bomb was taken out and cooled with water to room temperature. The content was centrifuged and washed repeatedly with deionized water. The solid product was dried in a vacuum oven at 50° C. before XRD pattern was taken. The XRD patterns are shown in FIG. 1 and the results are summarized in Table 2:

TABLE 2

| Run | DMECHA/ $SiO_2$ | $H_2O$/ $SiO_2$ | NaOH/ $SiO_2$ | Agitation | Time (days) | T° C. | Product |
|---|---|---|---|---|---|---|---|
| 1 | 0.22 | 9.70 | 0.045 | Tumbled | 3 | 170 | ZSM-12 |
| 2 | 0.22 | 17.9 | 0.091 | Static | 2 | 160 | ZSM-12 |
| 3 | 0.18 | 6.36 | 0.127 | Static | 5 | 150 | CHA + trace ZSM-12 |
| 4 | 0.18 | 6.36 | 0.109 | Tumbled | 3 | 150 | CHA + trace ZSM-12 |
| 5 | 0.18 | 6.36 | 0.091 | Tumbled | 3 | 150 | CHA |
| 6 | 0.18 | 6.36 | 0.091 | Tumbled | 5 | 150 | CHA + trace ZSM-12 |

The results show that when the temperature and/or water content is higher, pure ZSM-12 is obtained (Runs 1 and 2). When the water content and temperature are kept low, chabazite with a trace of ZSM-12 is produced (Runs 3 and 4). When the water content and temperature are kept low and the amount of NaOH is reduced, pure chabazite is produced after a crystallization time of 3 days (Run 5). Increasing the crystallization time to 5 days results in the formation of a trace amount of ZSM-12 (Run 6).

The chabazite product yield in Run 5 was 11.2 wt % based on the weight of synthesis mixture. Elemental analysis revealed the product to contain 0.56 wt % alumina, 72.5 wt % silica and 0.53 wt % Na (K below 0.01 wt %), indicating that the silica to alumina molar ratio of the chabazite product was 110.

EXAMPLE 3

Synthesis of High Silica Chabazite Using DMECHA Hydroxide

Run 5 of Example 2 was repeated but with the crystallization being repeated at 160° C. for 2 days. As shown in FIG. 2, the product was again pure chabazite. Elemental analysis revealed the product to contain 0.60 wt % alumina, 76.3 wt % silica, 0.33 wt % Na and 0.01 wt % K, indicating that the silica to alumina molar ratio of the chabazite product was 108. Increasing the crystallization time to 3 days again resulted in the formation of a trace amount of ZSM-12.

EXAMPLE 4

Synthesis of High Silica Chabazite Using DMECHA Fluoride Neutral Solution 6.326 ml of DMECHA$^+$ OH$^-$ (0.4252M) solution and 0.098 ml of HF (48 wt %) were pre-mixed to give a clear solution having a pH close to neutral (molar ratio: DMECHA$^+$ OH$^-$/HF=1). A 23.5 mg/ml aqueous solution of Al(NO$_3$)$_3$.9H$_2$O (0.344 ml) was added to the resultant DMECHA$^+$ F$^-$ solution followed by tetraethylorthosilicate (1.200 ml). The resultant mixture was sealed and continuously stirred for 18 hours (over night) at room temperature until all tetraethylorthosilicate was completely hydrolyzed. The resulted slurry was further homogenized by stirring and exposed to air for evaporation of water and ethanol until 1284 mg of thick slurry was obtained, which had the composition:

$SiO_2$:0.004$Al_2O_3$:0.5DMECHA:0.5F:5$H_2O$

Figures 4A, 4B, 4C, 4D, 4E, 4F, 4G:
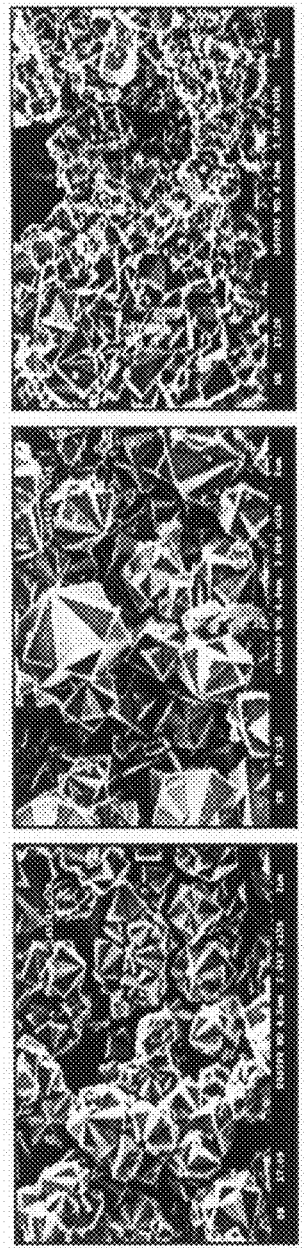
FIGS. 4(a) to 4(g) are SEM pictures of the products of Runs 1 to 7 respectively of Example 4.

LEV colloidal seeds (0.035 ml of a 14.1 wt. % aqueous suspension) were added to above slurry with mechanical mixing and the resulting mixture was transferred to a Teflon® lined 5 ml autoclave and crystallized at 185° C. for 65 hours under slow rotation (about 60 rpm). After this time, the resultant solids were recovered by centrifuging, washed with distilled water and dried at 100° C. to give about 334 mg of white microcrystalline solids (26% of yield based on the weight of the final slurry). XRD analysis on as-synthesized materials indicated an X-ray diffraction pattern associated with chabazite structure topology (FIG. 3(a)). SEM pictures show either cubic or twinned cubic crystal morphology having about 1 micron size (FIG. 4(a)).

As can be seen from Table 3, similar results were obtained when the synthesis of Example 4 was repeated using different silica sources, such as HiSil233, Silicic acid, Ultrasil, Cabosil, Ludox AS-30, and Ludox LS-30. XRD patterns of the as-synthesized materials are given in FIGS. 3(b) to (g) and SEM pictures are given in FIGS. 4(b) to (g). The particle sizes of the synthesized materials depended on the silica source. The products synthesized using HiSil233 and Silicic acid generally gave relatively large particle sizes (1-3 μm), whereas smaller particle sizes (0.2-0.4 μm) were obtained if Ultrasil, Cabosil, Ludox AS-30, and Ludox LS-3D were employed as silica sources.

TABLE 3

| Run | Silica source | Gel Si/Al$_2$ | Product | Yield (%) |
|---|---|---|---|---|
| 1 | TEOS | 250 | CHA (334 mg) | 26.0 |
| 2 | HiSil233 | 250 | CHA (343 mg) | 26.7 |
| 3 | Silicic acid | 250 | CHA (325 mg) | 25.3 |
| 4 | Ultrasil | 250 | CHA (336 mg) | 26.3 |
| 5 | Cabosil | 250 | CHA (332 mg) | 25.9 |
| 6 | Ludox AS-30 | 250 | CHA (400 mg) | 31.9 |
| 7 | Ludox LS-30 | 250 | CHA (414 mg) | 32.2 |

EXAMPLE 5

Synthesis of High Silica Chabazite Using Concentrated Solution of DMECHA Fluoride A high concentration solution of N,N,N-dimethylethylcyclohexyl ammonium fluoride (DMECHA$^+$ F$^-$) (3.650 g, 51.71 wt. %) was produced by evaporating water from the DMECHA$^+$F$^-$ solution produced in Example 5 and HiSil 233 (1.486 g) was then mechanically mixed with the resultant solution for a few of minutes to produce a stirrable homogeneous glue-like gel having the composition:

$SiO_2:0.002Al_2O_3:0.5DMECHA:0.5F:5H_2O$

LEV colloidal seeds (0.140 ml of a 14.1 wt. % aqueous suspension) were added to above gel added with mechanical mixing. The resulting gel mixture was transferred to Teflon® lined 25 ml stirred autoclave and crystallized at 185° C. for 65 hours under the condition of 300 rpm of stirring rate, 80 psi of N$_2$ fill pressure, and 2 hours of temperature ramp. The resultant solid was recovered by centrifuging, washed with distilled water and dried at 100° C. to give 1.411 g of white microcrystalline solid (27.5% of yield based on the weight of the final gel).

Figure 5:
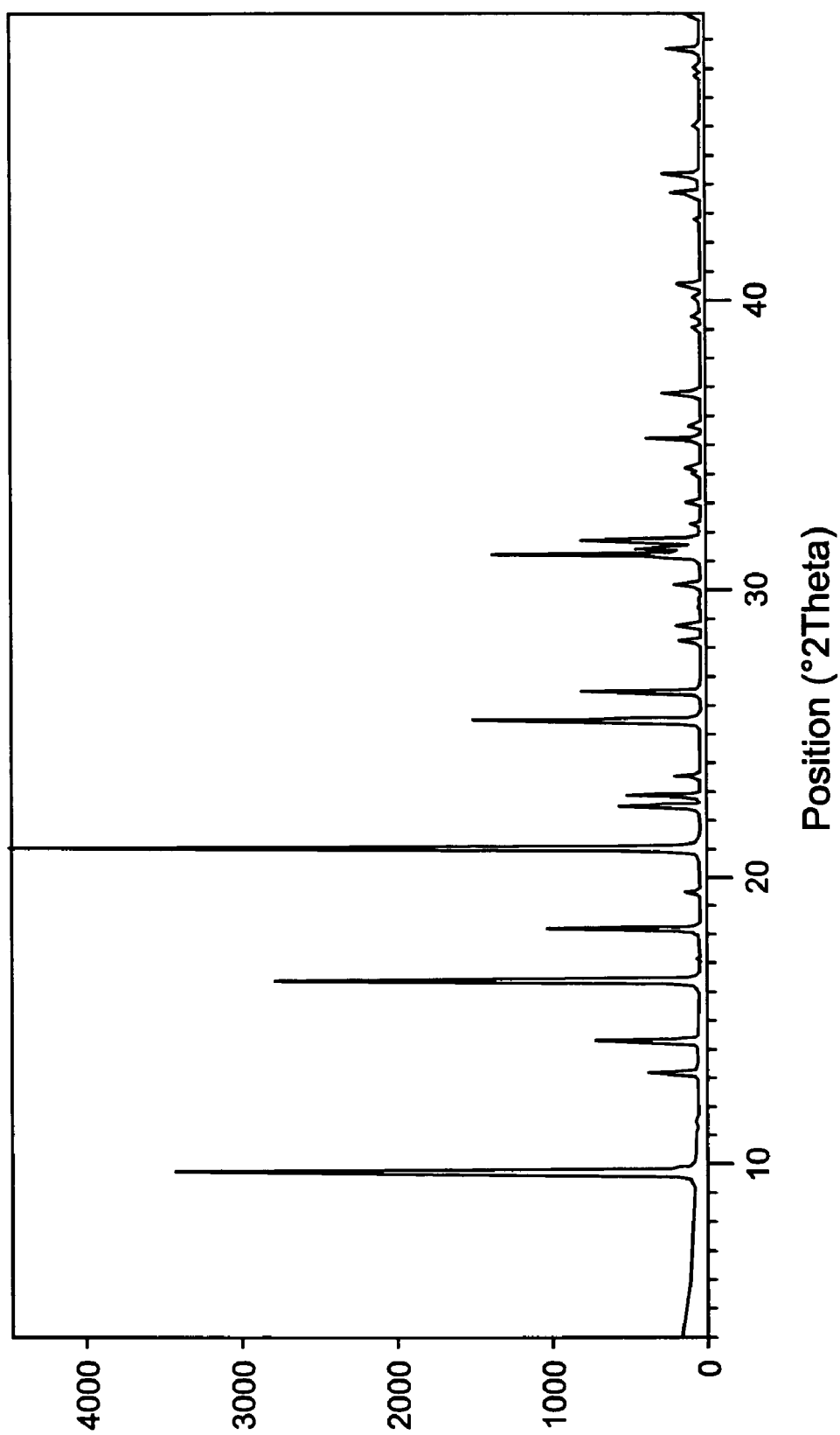
FIG. 5 is the X-ray diffraction pattern of the as-synthesized product of Example 5.
Figure 6:
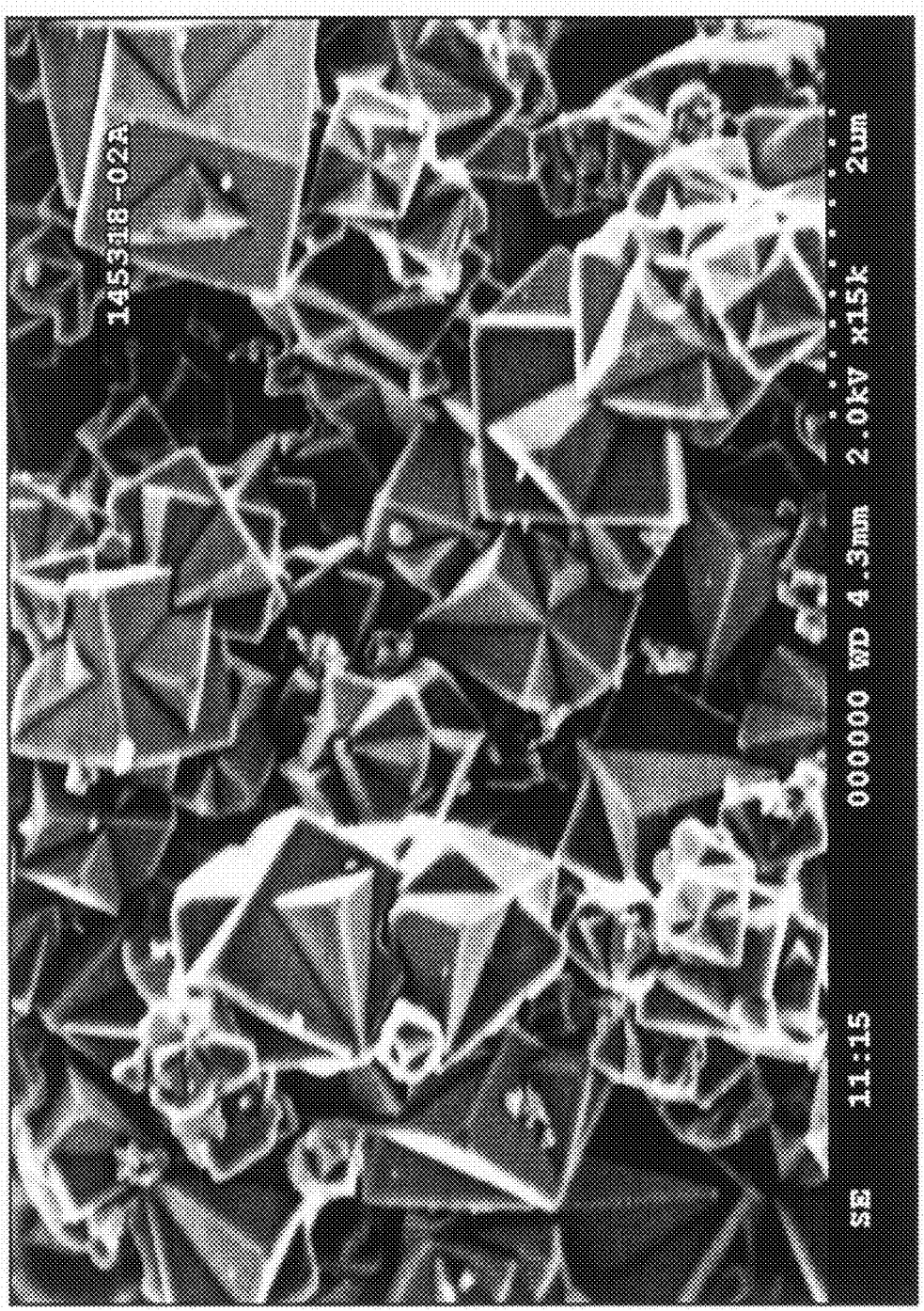
FIG. 6 is an SEM picture of the product of the Example 5.

XRD analysis of the as-synthesized material indicated an X-ray diffraction pattern associated with CHA structure topology (FIG. 5). SEM pictures show twinned cubic crystal morphology having 1.5-3 micron size, although trace amount of zeolite Beta (possible) can be observed in terms of different crystal morphologies (FIG. 6).

EXAMPLE 6

Synthesis of High Silica Chabazite Using Different Seeds

A 23.5 mg/ml aqueous solution of Al(NO$_3$)$_3$.9H$_2$O (2.148 ml) was added to an aqueous solution of N,N,N-dimethylethylcyclohexylammonium hydroxide (DMECHA$^+$ OH—) (18.45 ml, 0.7289M) followed by addition of tetraethylorthosilicate (6.000 ml). The resultant mixture was sealed and continuously stirred for 18 hours (over night) at room temperature until all tetraethylorthosilicate was completely hydrolyzed. To this clear solution was added 48 wt % aqueous solution of hydrofluoric acid (0.588 ml) which immediately resulted in a mixture slurry. This mixture slurry was further homogenized by stirring and exposed to air for evaporation of water and ethanol until a thick slurry mixture was obtained. Extra water was further evaporated under static conditions to give 6960 mg of a dry gel solid having the composition:

$SiO_2:0.0025Al_2O_3:0.5DMECHA:0.6F:6H_2O$

The above solid was divided into 6 approximately equivalent parts. To each of them was added with mechanical mixing 5 mg (0.4 wt % based on dry gel solid) of seeding material, SSZ-13 (CHA), SSZ-39 (AEI), Nu-3 (LEV), ERI, colloidal seeds (LEV), and SSZ-16 (AFX) respectively. The resulting mixture of solids were transferred to Teflon lined 5 ml autoclave and crystallized at 150° C. for 65 hours under slow rotation (about 60 rpm). After this time, the resultant solids were recovered by centrifuging, washed with distilled water and dried at 100° C. to give about 310 mg of white microcrystalline solids for each reaction (27% of yield based on the weight of the dry gel).

XRD analysis on as-synthesized materials indicated an X-ray diffraction pattern associated with chabazite structure topology. SEM pictures show either cubic or twinned cubic crystal morphology having 1-10 micron size, which depend on different kinds of seeding materials used.

Similar syntheses and results could also be produced by using N,N,N-methyldiethylcyclohexylammonium hydroxide (MDECHA$^+$ OH$^-$), N,N,N-triethylcyclohexylammonium hydroxide (TECHA$^+$ OH$^-$), and 2,7-Dimethyl-1-azonium [5.4]decane hydroxide(DM27AD$^+$ OH$^-$), as templates.

EXAMPLE 7

Synthesis of High Silica Chabazite at High Dilution

A series of fluoride-free reaction mixtures comprising N,N,N-trimethyladamantylammonium hydroxide (TMAA$^+$ OH$_-$, 0.57 molar aqueous solution, 0.2 molar equivalent), silica source, Al(NO$_3$)$_3$.9H$_2$O (amount based on desired Si/Al ratio), colloidal LEV seeds (0.1-0.5 wt %), and water (such that H$_2$O/SiO$_2$=10-40) were prepared and each was sealed in a reactor and crystallized at 150° C. or 170° C. for 3 days under slow rotation (about 60 rpm). After this time, the resultant solids were recovered by centrifuging, washed with distilled water and dried at 100° C. The isolated solids were characterized by X-ray diffraction, scanning electron microscopy and electron diffraction and were identified as high Si/Al chabazite.

The results are summarized in Table 4, together with the results of similar tests conducted with a reaction mixture having the same composition as that described above but also containing boric acid as a boron source and/or 0.2 molar equivalent of HF. It will be seen that at the high H$_2$O/SiO$_2$ value used in the tests, high silica chabazite was produced both with and without boron in the reaction mixture and at crystallization temperatures of both 150° C. and 170° C., provided HF was not added to the reaction mixture. In contrast, the addition of HF to the reaction mixture produced a product that was largely amorphous and contained only trace amounts of the desired chabazite.

TABLE 4

| Silica Source | Si/Al | Si/B | HF | H$_2$O/SiO$_2$ | Cryst. Temp. | Product |
|---|---|---|---|---|---|---|
| Ultrasil | 303 | 0 | 0 | 22 | 170° C. | CHA |
| Cabosil | 303 | 0 | 0 | 22 | 170° C. | CHA |
| Ultrasil | 303 | 100 | 0 | 22 | 170° C. | CHA |
| Ultrasil | 303 | 100 | 0 | 22 | 170° C. | CHA |
| Ultrasil | 303 | 0 | 0 | 22 | 150° C. | CHA |
| Ultrasil | 303 | 100 | 0 | 22 | 150° C. | CHA |
| Ultrasil | 303 | 0 | 0.2 | 22 | 150° C. | Amorphous + trace CHA |
| Ultrasil | 303 | 100 | 0.2 | 22 | 150° C. | Amorphous + trace CHA |

While the present invention has been described and illustrated by reference to particular embodiments, those of ordinary skill in the art will appreciate that the invention lends itself to variations not necessarily illustrated herein. For this reason, then, reference should be made solely to the appended claims for purposes of determining the true scope of the present invention.

What is claimed is:

1. A method of synthesizing a crystalline material comprising a CHA framework type molecular sieve and having a composition involving the molar relationship:

(n)X$_2$O$_3$:YO$_2$ wherein X is a trivalent element; Y is a tetravalent element; and n is from 0 to less than 0.01, the method comprising:
  (a) preparing a reaction mixture capable of forming the crystalline material, the reaction mixture comprising a source of water, a source of an oxide of a tetravalent element Y and optionally a source of an oxide of a trivalent element X, wherein the reaction mixture is substantially free of fluoride ions added as HF and further comprises an organic directing agent for directing the formation of a CHA framework type molecular sieve and having the formula:

[R$^1$R$^2$R$^3$N—R$^4$]$^+$ Q$^-$ wherein R$^1$ and R$^2$ are joined to form a substituted or unsubstituted five-membered nitrogen-containing heterocyclic ring, and wherein R$^3$ and R$^4$ are hydrocarbyl groups joined to form a substituted or unsubstituted six-membered nitrogen-containing heterocyclic ring; and Q$^-$ is an anion;
  (b) maintaining the reaction mixture under conditions sufficient to form crystals of the crystalline material; and
  (c) recovering the crystalline material from (b).

2. The method of claim 1, wherein the reaction mixture is substantially free of all fluoride ions; wherein the crystalline material is substantially free of framework phosphorus; wherein n is from about 0.0005 to about 0.007; wherein Y is silicon, tin, titanium, germanium or a combination thereof and wherein X is aluminum, boron, iron, indium, gallium or a combination thereof.

3. The method of claim 1 wherein [R$^1$R$^2$R$^3$N—R$^4$]$^+$ is 2,7-dimethyl-1-azonium[5,4] decane.

4. The method of claim 1 wherein the reaction mixture has the following molar composition:

| | |
|---|---|
| H$_2$O/YO$_2$ | 0.1 to 40 |
| OH/YO$_2$ | 0 to 2 |
| R/YO$_2$ | 0.01 to 2 |
| X$_2$O$_3$/YO$_2$ | 0 to 0.1 | where R is said organic directing agent, and wherein the H$_2$O/YO$_2$ molar ratio is from about 10 to about 40.

5. The method claim 1 wherein the reaction mixture comprises from about 0.01 ppm by weight to about 10,000 ppm by weight of seeds, and wherein the seeds comprise a crystalline material having at least one of an AEI, LEV, CHA, ERI, AFX or OFF framework-type.

6. The method claim 1 wherein the reaction mixture further comprises a second organic directing agent for directing the formation of an AEI framework type molecular sieve.

7. The method claim 6 wherein said second organic directing agent comprises an N,N-diethyl-2,6-dimethylpiperidinium compound.

8. A process for producing olefins comprising contacting an organic oxygenate compound under oxygenate conversion conditions with a catalyst comprising a crystalline material produced by the method of claim 1.

9. The method of claim 8 wherein the olefins comprise at least one of ethylene and propylene, and wherein the method further comprises polymerizing the olefins to make (i) a polyethylene polymer and/or copolymer, and/or (ii) a polypropylene polymer and/or copolymer.

10. A method of synthesizing a crystalline material comprising a CHA framework type molecular sieve and having a composition involving the molar relationship:

(n)X$_2$O$_3$:YO$_2$ wherein X is a trivalent element; Y is a tetravalent element; and n is from 0 to less than 0.01, the method comprising:
  (a) preparing a reaction mixture capable of forming the crystalline material, the reaction mixture comprising at least one directing agent, a source of water, a source of an oxide of a tetravalent element Y and optionally a source of an oxide of a trivalent element X, wherein the reaction mixture is substantially free of fluoride ions added as HF and has an H$_2$O:YO$_2$ molar ratio of greater than 20, the at least one directing agent selected from N,N,N-dimethylethylcyclohexylammonium, N,N,N-methyldiethylcyclohexylammonium, and N,N,N-triethylcyclohexylammonium, and wherein the reaction mixture has the following molar composition:

| | |
|---|---|
| H$_2$O/YO$_2$ | greater than 20 to 40 |
| OH/YO$_2$ | 0 to 2 |
| R/YO$_2$ | 0.01 to 2 |
| X$_2$O$_3$/YO$_2$ | 0 to 0.01 | where R is the organic directing agent;
  (b) maintaining the reaction mixture under conditions sufficient to form crystals of the crystalline material; and
  (c) recovering the crystalline material from (b).

11. The method of claim 10, wherein the reaction mixture is substantially free of all fluoride ions, wherein the crystalline material is substantially free of framework phosphorus; wherein n is from about 0.0005 to about 0.007; wherein Y is silicon, tin, titanium, germanium or a combination thereof and wherein X is aluminum, boron, iron, indium, gallium or a combination thereof.

12. The method claim 10 wherein said reaction mixture comprises from about 0.01 ppm by weight to about 10,000 ppm by weight of seeds, wherein the seeds comprise a crystalline material having at least one of an AEI, LEV, CHA, ERI, AFX or OFF framework-type.

13. The method of claim 10 wherein said reaction mixture further comprises a second organic directing agent for directing the formation of an AEI framework type molecular sieve.

14. The method claim 13 wherein the second organic directing agent comprises a substituted piperidine or piperidinium compound.

15. A method of synthesizing a crystalline material comprising a CHA framework type molecular sieve which is free of stacking faults and/or any intergrown phase with an AEI framework type molecular sieve, the crystalline material having a composition involving the molar relationship:

(n)X$_2$O$_3$:YO$_2$ wherein X is a trivalent element; Y is a tetravalent element; and n is from 0 to less than 0.01, and wherein said crystalline material is substantially free of framework phosphorus, the method comprising:
  (a) preparing a reaction mixture capable of forming the crystalline material, the reaction mixture comprising at least one structure directing agent, a source of water, a source of an oxide of a tetravalent element Y and optionally a source of an oxide of a trivalent element X, wherein the reaction mixture is substantially free of fluoride ions added as HF, wherein the structure directing agent comprises a compound having the formula $[R^1R^2R^3N\text{---}R^4]^+ Q^-$ wherein $R^1$ and $R^2$ are independently selected from a methyl group and an ethyl group, wherein $R^3$ is an ethyl group, and wherein $R^4$ is a cyclohexyl group, and $Q^-$ is an anion, and wherein said reaction mixture comprises from about 0.01 ppm by weight to about 10,000 ppm by weight of seeds, wherein the seeds comprise a crystalline material having at least one of an AEI, LEV, CHA, ERI, AFX or OFF framework-type;

(b) maintaining the reaction mixture under conditions sufficient to form crystals of the crystalline material; and (c) recovering the crystalline material from (b).

16. The method of claim 15 wherein the reaction mixture has the following molar composition:

| | |
|---|---|
| $H_2O/YO_2$ | 0.1 to 40 |
| $OH/YO_2$ | 0 to 2 |
| $R/YO_2$ | 0.01 to 2 |
| $X_2O_3/YO_2$ | 0 to 0.1 | where R is the organic directing agent.

17. The method of claim 15 wherein Y is silicon, tin, titanium, germanium or a combination thereof; and wherein X is aluminum, boron, iron, indium, gallium or a combination thereof.

18. The method of claim 15 wherein Y is silicon, and X is aluminum.

19. The method of claim 15, wherein n ranges from about 0.0005 to about 0.007.

20. A method of synthesizing a crystalline material comprising a CHA framework type molecular sieve which is free of stacking faults and/or any intergrown phase with an AEI framework type molecular sieve, the crystalline material having a composition involving the molar relationship:

$$(n)X_2O_3{:}YO_2$$

wherein X is a trivalent element; Y is a tetravalent element; and n is from 0 to less than 0.01, and wherein said crystalline material is substantially free of framework phosphorus, the method comprising:

(a) preparing a reaction mixture capable of forming the crystalline material, the reaction mixture comprising at least one structure directing agent, a source of water, a source of an oxide of a tetravalent element Y and optionally a source of an oxide of a trivalent element X, wherein the reaction mixture is substantially free of fluoride ions added as HF, wherein the structure directing agent comprises a compound having the formula $[R^1R^2R^3N\text{---}R^4]^+ Q^-$ wherein $R^1$ and $R^2$ are independently selected from a methyl group and an ethyl group, wherein $R^3$ is an ethyl group, and wherein $R^4$ is a cyclohexyl group, and $Q^-$ is an anion;

(b) maintaining the reaction mixture under conditions sufficient to form crystals of the crystalline material; and (c) recovering the crystalline material from (b).

* * * * *